(12) United States Patent
Shin et al.

(10) Patent No.: US 12,359,172 B2
(45) Date of Patent: Jul. 15, 2025

(54) METHOD FOR PREPARING 3D CARTILAGE ORGANOID BLOCK

(71) Applicant: XCELL THERAPEUTICS INC., Seoul (KR)

(72) Inventors: Young Key Shin, Seoul (KR); Sang Gyu Park, Gyeonggi-do (KR); Young Deug Kim, Gyeonggi-do (KR); Jong Chan Ahn, Gyeonggi-do (KR); Byoung Jun Park, Gyeonggi-do (KR); Ui Il Lee, Seoul (KR)

(73) Assignee: XCELL THERAPEUTICS INC., Seoul (KR)

( * ) Notice: Subject to any disclaimer, the term of this patent is extended or adjusted under 35 U.S.C. 154(b) by 0 days.

(21) Appl. No.: 16/067,761

(22) PCT Filed: Oct. 1, 2016

(86) PCT No.: PCT/KR2016/011037
§ 371 (c)(1),
(2) Date: Jul. 2, 2018

(87) PCT Pub. No.: WO2017/115982
PCT Pub. Date: Jul. 6, 2017

(65) Prior Publication Data
US 2019/0010459 A1 Jan. 10, 2019

(30) Foreign Application Priority Data

Dec. 30, 2015 (KR) .......................... 10-2015-0189505

(51) Int. Cl.
| | |
|---|---|
| *C12N 5/077* | (2010.01) |
| *A61K 35/28* | (2015.01) |
| *A61K 35/32* | (2015.01) |
| *A61L 27/38* | (2006.01) |
| *C12N 5/071* | (2010.01) |

(52) U.S. Cl.
CPC ............ *C12N 5/0655* (2013.01); *A61K 35/28* (2013.01); *A61K 35/32* (2013.01); *A61L 27/3834* (2013.01); *A61L 27/3852* (2013.01); *A61L 27/3895* (2013.01); *C12N 5/0671* (2013.01); *A61L 2430/06* (2013.01); *C12N 2506/13* (2013.01); *C12N 2506/1346* (2013.01); *C12N 2513/00* (2013.01)

(58) Field of Classification Search
CPC ................ C12N 5/0655; C12N 5/0671; C12N 2506/13; C12N 2506/1346; C12N 2513/00; A61K 35/28; A61K 35/32; A61L 27/3834; A61L 27/3852; A61L 27/3895; A61L 2430/06
See application file for complete search history.

(56) References Cited

FOREIGN PATENT DOCUMENTS

| KR | 20070113572 A | 11/2007 |
|---|---|---|
| KR | 20110005192 A | 1/2011 |

OTHER PUBLICATIONS

Solid preform fabricated scaffolds designed to carry multicellular mesenchymal stem cell spheroids for cartilage regeneration. Huang et al. European Cells and Materials 26 (2013): 179-194).*
Steck et al. "Induction of intervertebral disc-like cells from adult mesenchymal stem cells." Stem cells 23.3 (2005): 403-411 (Year: 2005).*
Sart et al. "Three-dimensional aggregates of mesenchymal stem cells: cellular mechanisms, biological properties, and applications." Tissue Engineering Part B: Reviews 20.5 (2014): 365-380 (Year: 2014).*
Ishihara et al. "Simultaneous regeneration of full-thickness cartilage and subchondral bone defects in vivo using a three-dimensional scaffold-free autologous construct derived from high-density bone marrow-derived mesenchymal stem cells." Journal of orthopaedic surgery and research 9 (2014): 1-10 (Year: 2014).*
Beachley et al., "The Fusion of Tissue Spheroids Attached to Pre-Stretched Electrospun Polyurethane Scaffolds," Journal of Tissue Engineering, 2014, 5:1-11, 11 pages.
Fennema, et al., "Spheroid Culture as a Tool for Creating 3D Complex Tissues," Trends in Biotechnology, 2013, 31 (2):108-115, 8 pages.
Fleming et al., "Fusion of Uniluminal Vascular Spheroids: A Model for Assembly of Blood Vessels," Dev Dyn., 2010, 19 pages.

* cited by examiner

*Primary Examiner* — Fereydoun G Sajjadi
*Assistant Examiner* — Alexander W Nicol
(74) *Attorney, Agent, or Firm* — LEX IP MEISTER, PLLC

(57) ABSTRACT

The present invention is to provide a 3D cartilage organoid block prepared by differentiating mesenchymal stem cells into 3D spheroid cartilage tissues, a basic unit for the 3D cartilage spheroid block. The inventors found that both the amount of GAG matrix and the expression of the collagen type2 increased. Therefore, the method of this invention provides clinically applicable cartilage tissues by effectively enhancing the function of the cartilage differentiation constructs according to 2D culture. The 3D cartilage organoid block can be usefully applied to the area, such as, articular cartilage regeneration and plastic surgery, where cartilage tissues restoration is required.

3 Claims, 2 Drawing Sheets
Specification includes a Sequence Listing.

[Fig. 1]
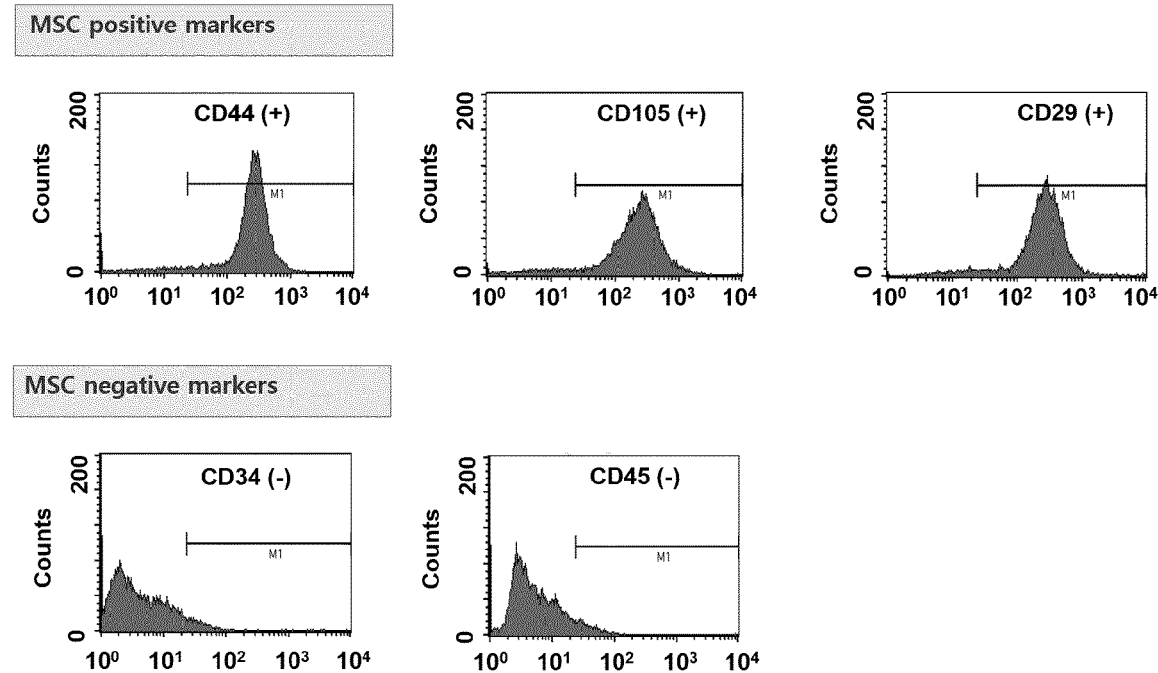
[Fig. 2]
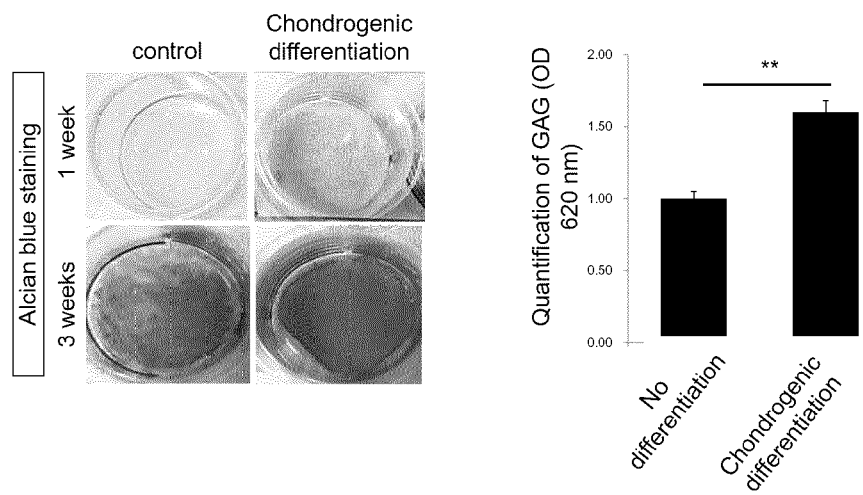
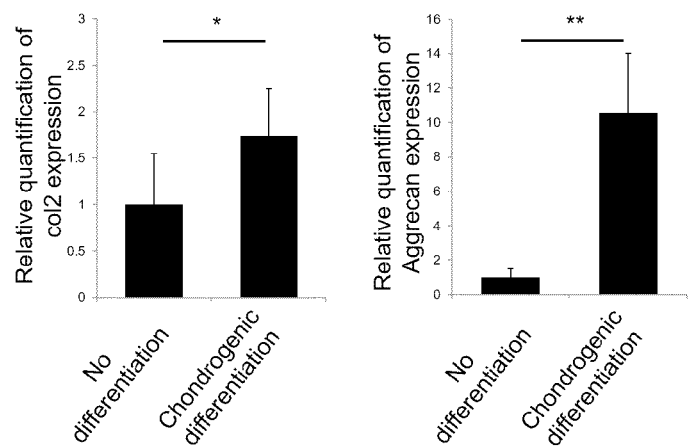

[Fig. 3]
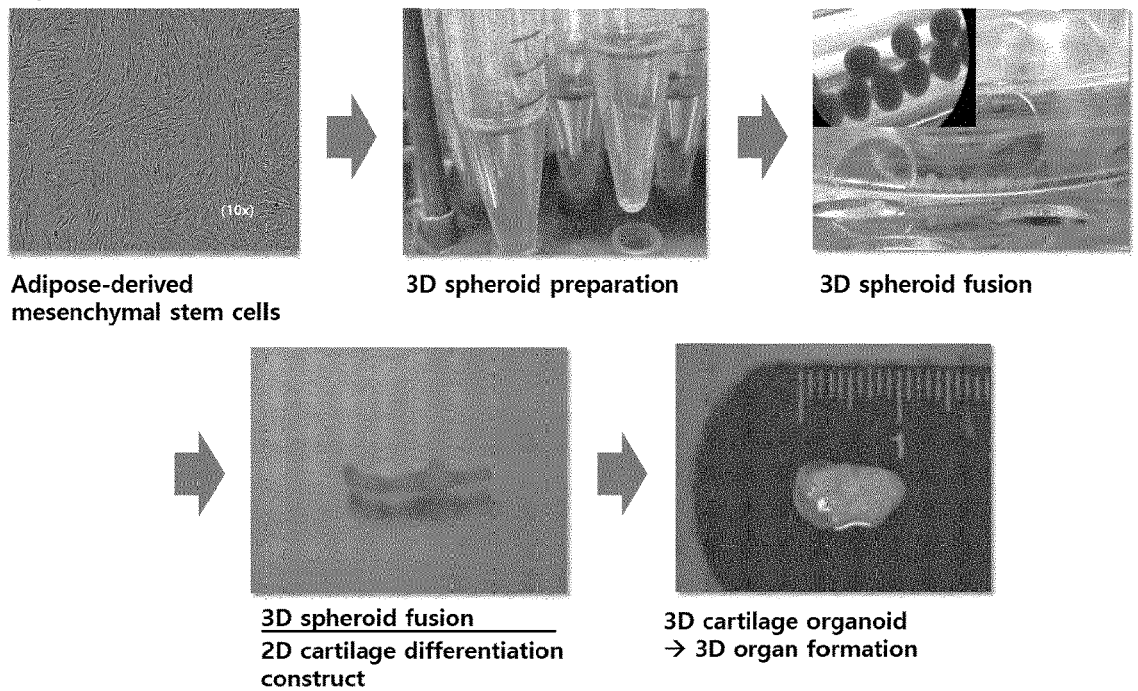
Adipose-derived mesenchymal stem cells → 3D spheroid preparation → 3D spheroid fusion → 3D spheroid fusion 2D cartilage differentiation construct → 3D cartilage organoid → 3D organ formation
[Fig. 4]
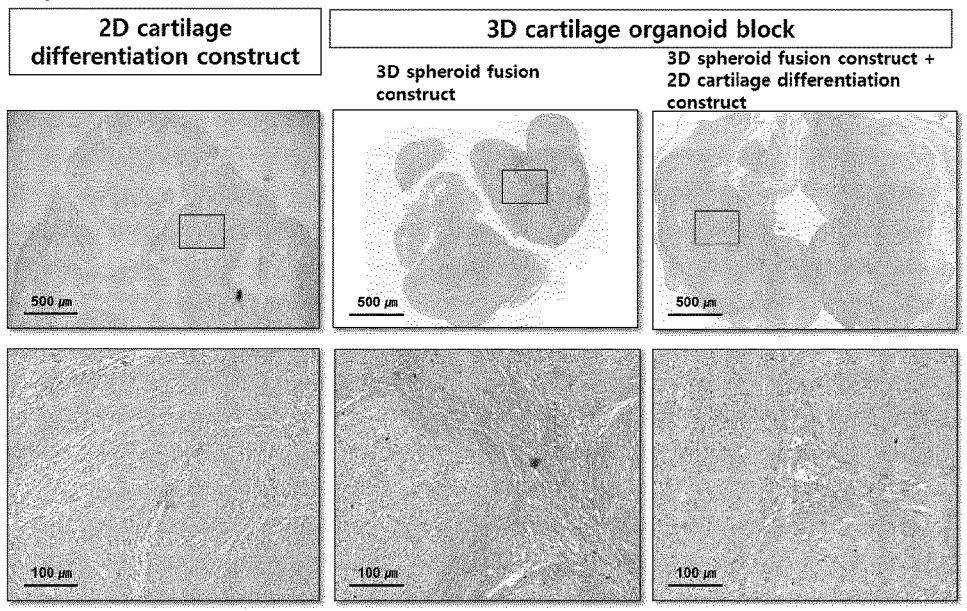
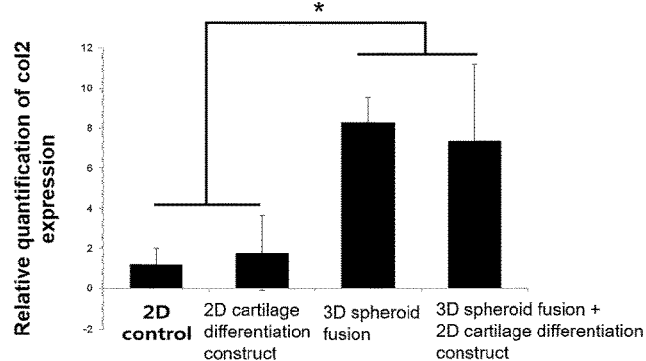

METHOD FOR PREPARING 3D CARTILAGE ORGANOID BLOCK

CROSS-REFERENCES TO RELATED APPLICATIONS

This application is a U.S. national phase application, pursuant to 35 U.S.C. § 371, of PCT/KR2016/011037, filed Oct. 1, 2016, designating the United States, which claims priority to Korean Application No. 10-2015-0189505, filed Dec. 30, 2015. The entire contents of the aforementioned patent applications are incorporated herein by reference.

TECHNICAL FIELD

The present invention relates to preparing artificial tissues. The present invention is directly related to a method for preparing artificial cartilage tissues in vitro.

BACKGROUND ART

Aging and the increases of social and physical activities have resulted in the increase of the number of patients suffering from cartilage lesions, and thereby the need for the development of medical technologies to restore the damaged cartilage has also increased. However, since the cartilage tissue has no blood vessels and the cartilage cell's mobility is limited by extracellular matrix (ECM), it is difficult to regenerate the damaged cartilage without efforts.

Among the current methods for treating damaged cartilage, artificial joints replacement has advantages of pain relief and making the patient walk naturally when successful surgical operation is achieved. Since the technologies relating to artificial joints replacement have been improved a lot recently, artificial joints replacement surgery is carried out for the treatment of heavily damaged cartilage. In addition, minimally invasive artificial joints replacement surgery contributes to the lifespan expansion of the artificial joints and rapid recovery from the surgery. However, artificial joint surgery is a burden on the patients yet in various aspects. The abrasion of artificial joints limits the lifespan of the artificial joints, and the durability depends on the management and the result of surgery. Further, reoperation will be required, if there is bacterial infection during the surgery. Further, a risk of an adverse effect or a complication exists during bone cutting operation. Therefore, the need for regenerative medical solutions, which employee cells, has been continuously raised. In this regard, autologous cartilage cell implantation (aci) using the cells obtained from the patients themselves, heterologous cartilage cell implantation, and researches to develop a therapeutic agent by differentiating autologous and/or heterologous stem cells into cartilage cells have been developed.

Autologous and/or heterologous cartilage cell implantion has a problem of dedifferentiation resulting from cartilage cell culturing, and thus it is not possible to obtain enough number of cells for the effective treatment. The treatment using mesenchymal stem cells has an advantage of providing enough number of cells. Even though there is no perfect cartilage differentiation method yet, numerous technologies have been developed recently. The technologies including, such as, chondrocytes viability enhancement, phenotype maintenance, and physical strength maintenance, should be developed to make the treating methods using the cells be successful. Until now, various methods, for example, enhancing cell adhesion rate by the use of 3D supports, such as, hydrogel, maintaining more natural cartilage tissues through controlling surrounding microenvironment, retaining elasticity to external pressure, have been introduced to overcome the problems above mentioned (Korean Patent Registration No. 10-1367221). However, the problems, such as, interaction between cells and biomaterials, biocompatibility, and, in particular, binding with neighboring cartilages, have not yet been solved.

These days, cells are prepared as a high density 3D pellet, without using a support. This method of spheroid forming has advantages of simple preparation process and easy reproducibility. Though cell mass culture technology using 96 well, which comprises one spheroid in every single well, was developed, it is very difficult to form a structurally one tissue where the spheroids are fused to each other. It is not possible to prepare cartilage tissues with biomaterials, such as, hydrogel, and thus it is difficult to make a treating agent with the conventional technologies. KR Patent No. 10-1109668 discloses that bone differentiation from adipose stem cells using mesoporous PLGA-silica scaffold for tissue engineering, KR Patent No. 10-0839875 discloses an invention about a scaffold for the regeneration of an articular cartilage, wherein the scaffold is prepared by seeding cells into a mesoporous scaffold comprising biodegradable polymers and phosphatic calcium biocompatible ceramics.

DISCLOSURE OF INVENTION

Technical Problem

We, inventors have studied novel methods for preparing 3 dimensional cartilage organoid block to address the problems mentioned above. As a result, we first found that, in case 3D spheroid cartilage tissues contacting to each other were differentiated into a cartilage, the tissues were connected to each other to provide a large 3D cartilage organoid block. Second, we found that 2D high density cartilage differentiation cells layer was self-assembled to surround 3D spheroid cartilage tissues and thus structurally dense 3D cartilage organoid block was formed, when cartilage differentiation was continuously induced by loading 3D spheroidal cartilage tissues (mesenchymal stem cell constructs or constructs in the intermediate steps of differentiation of mesenchymal stem cells into cartilage cells) on the central part of the 2D high density cartilage differentiation cells layer (mesenchymal stem cells or cells layer in the intermediate status of cartilage cell differentiation from mesenchymal stem cells).

In this regard, the present invention provides a method of preparing 3D cartilage organoid block either by fusing and connecting 3D spheroid cartilage tissues themselves, or by inducing self-assembly of 2D cartilage differentiation cells layer in the presence of 3D spheroid cartilage tissues which are prepared by the differentiation of mesenchymal stem cells to 3D spheroid state cartilage tissues, wherein the 2D cartilage cells layer are prepared by the differentiation of mesenchymal stem cells to high density cartilage tissues on 2D plate.

In addition, the purpose of the present invention is to use the 3D cartilage organoid block to any area or field where cartilage restoration is required.

Solution to Problem

The purpose of the present invention is to provide a method of preparing 3D cartilage organoid block, which comprises the steps of, (a) differentiating mesenchymal stem cells to 3D spheroidal cartilage tissues by 3D culture of the mesenchymal stem cells; (b) differentiating mesenchymal stem cells to a 2D cartilage differentiation cells layer by 2D culture of the mesenchymal stem cells; and (c) incubating the 3D spheroidal cartilage tissues on the 2D cartilage differentiation cells layer to induce self-assembly.

The mesenchymal stem cells include the cells derived from adipose, bone marrow, cord, cord blood, placenta, synovium, periosteum, perichondrium, tonsil, skin, hair follicle, peripheral blood, muscle, liver, neuron tissue, fetal membrane, amnion, meniscus or anterior cruciate ligament.

The method of the present invention further includes a step of preparing 3D spheroid fusion constructs by the fusion and culture of 3D spheroid cartilage tissues.

The 3D spheroid fusion constructs can be prepared by natural fusion, fusion using biocompatible glue, or fusion using a stitching fiber. The 3D spheroid fusion constructs can be prepared by the fusion and culture of different 3D spheroid cartilage tissues, with the use of biocompatible polymer scaffold containing a 3D spheroid.

Advantageous Effects of Invention

The present invention provides structurally large and dense, and functionally effective 3D cartilage tissues, which is used for the preparation of 3D cartilage organoids, in comparison to the conventional cartilage differentiation methods. Furthermore, more human-like cartilage tissues can be prepared by the fusion of self-assembly of 3D spheroid cartilage tissues which is considered as a small functional unit. Further, the present invention incorporates advantageous features of the conventional cartilage differentiation methods. Specifically, high density 2D cartilage differentiation cells layer is detached from the plate through self-assembly and thus contains the cells own ECM, which results in effective filling the gaps between 3D spheroid cartilage tissues and increasing biocompatibility thereof. Further, since the 3D spheroid cartilage tissue is structurally dense, it functions as a backbone to enhance the strength. In this regard, the present invention makes it possible to prepare a treating agent which enhances strength and increases biocompatibility when it is implanted to the part of the cartilage lesion of a patient or the portion of a body where additional cartilage is necessary.

BRIEF DESCRIPTION OF DRAWINGS

FIG. 1 shows FACS analysis results of 3 stem cell positive markers [CD44(+), CD105(+), CD29(+)] and 2 negative markers [CD34(−), CD45(−)] to assess mesenchymal stem cells stemness.

FIG. 2 shows the results of qRT-PCR analysis of the expression of the ECM marker (col2, aggrecan). The mesenchymal stem cells were differentiated into cartilage cells under 2D culture conditions, and the expression of the cartilage differentiation marker, GAG, was quantitatively analyzed using Alcian blue staining.

FIG. 3 shows the overall process for preparing 3D cartilage organoids, wherein 3D spheroid cartilage tissues are produced from adipose-derived mesenchymal stem cells.

FIG. 4 is the results of Alcian blue immune staining (A) and qRT-PCR for collagen type II (B), for the assessment of cartilage differentiation capacity of 3D spheroid fusion constructs and 3D cartilage organoids, respectively.

BEST MODE FOR CARRYING OUT THE INVENTION

The present invention relates to a method for preparing a 3D cartilage organoid block, which is characterized by (a) 3D culturing and differentiating mesenchymal stem cells to 3D spheroid cartilage tissues; (b) 2D culturing and differentiating mesenchymal stem cells to a 2D cartilage differentiation cells layer; and (c) incubating the 3D spheroid cartilage tissues on the 2D cartilage differentiation cells layer to induce self-assembly.

In the present invention, the term "2D cell culture" means that cells are incubated in one layer on a plate, and the term "3D culture" means that cells are 3 dimensionally incubated with other neighboring cells. The said mesenchymal stem cells includes the cells derived from asipose, bone marrow, cord, cord blood, placenta, synovia, periosteum, or perichondrium.

In the present invention, the term "cartilage cell" refers to a cartilage cell obtained by the differentiation of a stem cell of an animal including human, and further includes a cartilage cell cultured from cartilage tissue. The said stem cell preferably means adult mesenchymal stem cell, embryonic stem cell, pluripotent stem cell, and undifferentiated progenitor cell, etc. The said cartilage cell preferably means a cartilage cell in vitro obtained from human cartilage tissue, and more preferably mentions a cartilage cell in vitro obtained from human normal cartilage vitrification.

This invention may further includes a step of preparing a fusion construct by the fusion and culture of the 3D spheroid cartilage tissues, in addition to the steps of (a) 3D culturing and differentiating mesenchymal stem cells to 3D spheroid cartilage tissue; (b) 2D culturing and differentiating mesenchymal stem cells to a 2D cartilage differentiation cells layer; and (c) inducing incubating the 3D spheroid cartilage tissues on the 2D cartilage differentiation cells layer to induce self-assembly.

In addition, the said 3D spheroid fusion construct can be prepared by natural fusion, fusion by the use of biocompatible glue or a stitching fiber, or can be prepared by the fusion and culture of the different 3D spheroid tissues using a biocompatible polymer scaffold harboring the 3D spheroids.

In the present invention, a method for preparing an organoid for cartilage tissues is provided, wherein the cartilage tissues are prepared by self-assembly without using a scaffold. Although the 3D cartilage organoid block of the present invention basically prefers a method which does not employ a scaffold, it does not preclude the use of appropriate biocompatible scaffold. The method for preparing a 3D spheroid fusion construct by the use of 3D spheroid cartilage tissue as a basic unit comprises the methods of (i) natural fusion of the 3D spheroid cartilage tissues themselves, (ii) connecting 3D spheroid cartilage tissues after applying biocompatible glue on the tissues, (iii) using both biocompatible polymer scaffold and 3D cartilage tissues, (iv) making a frame with a suture thread and then connecting the 3D spheroid cartilage tissues on the frame, and (v) preparing free-formed constructs (fusion constructs) by passing through the 3D spheroid cartilage tissues with a suture thread.

The method (i) above utilizes a natural event that if the 3D spheroid cartilage tissues are contacted to each other, then ECMs are externally secreted from the cartilage tissues and the secreted ECMs are connected to each other, and thereby the respective cartilage tissues form a construct (fusion construct) without artificial manipulation.

As for the method (ii) above, the biocompatible glue for medical use imitates the features of ECM, and has an advantage of rapidly attaching the respective 3D spheroid cartilage tissues. The natural glue includes fibrin glue, gelatin glue, alginates glue, and hyaluronic acid glue, and synthetic polymer glue.

According to the method (iii) above, the 3D spheroid fusion construct can be made by the use of a biocompatible polymer which can contain 3D spheroid cartilage tissues. This method has a specific effect to enhance the strength of the 3D fusion constructs.

According to the method (iv) above, a frame having a specific form is prepared using medical suture thread, and then 3D spheroid cartilage tissues are loaded on the frame above to provide 3D spheroid fusion constructs. The frame can be a net type, a linear array type, or a spiral type, but not limited to these types. This method is effective to make 3D spheroid fusion construct having a specific form.

In accordance with the method (v), various forms of 3D spheroid fusion constructs can be made by penetrating the 3D spheroid with a medical suture thread as sewing. This method provides various forms of cartilage block constructs, and thus the application value of the 3D spheroid fusion constructs advantageously increases.

The 3D cartilage organoid block of the present invention can be easily prepared by any person, since the preparation method is simple. The results of Alcian blue staining represented increased amount of GAG matrix and increased expression of collagen 2, an indicator of a normal cartilage cell, which support that normal cartilage tissues were formed well.

MODE FOR THE INVENTION

The following examples provide illustrative embodiments. In light of the present disclosure and the general level of skill in the art, those of skill will appreciate that the following examples are intended to be exemplary only and that numerous changes, modifications, and alterations can be employed without departing from the scope of the presently claimed subject matter.

Example 1. Isolation of Human Mesenchymal Stem Cells, Incubation and Assessment of Stemness Adipose tissues were cut to small pieces with a mess, and then the obtained pieces were washed three times with phosphate buffered saline (PBS)(Sigma, St. Louis, MO). Then, the small pieces of adipose tissues were put into a 50 ml conical tube. PBS was added to the tube and stirring was carried out, and then centrifuged. The soup was discarded, and Dulbecco's modified Eagle medium (DMEM) was added up to a volume of 50 ml, and thereafter the mixture was allowed to react for 90 minutes at 37° C. Unsolved adipose tissues suspended in the upper layer was removed after centrifugation for 10 minutes at 2,000 rpm. Then, washing with DMEM, centrifugation and removal were repeated. The isolated adipose-derived stem cells were incubated and proliferated with serum-free stem cell culture medium (chemically defined media) at 37° C. in a 5% $CO_2$ incubator. The DMEM including 10% FBS can be used for the proliferation. The proliferated mesenchymal stem cells were analyzed by detecting stem positive antigen markers, CD44, CD105 and CD29s and stem negative antigen markers, CD34 and CD45, with Fluorescence-activated cell sorting (FACS).

Example 2. The Assessment of Differentiation of Mesenchymal Stem Cells into Cartilage The obtained stem cells were seeded at $1\times10^4$ cells/cm$^2$ and incubated at 37° C. in a 5% $CO_2$ incubator, while the cells were treated with cartilage differentiation medium every 2 days, in order to differentiate the mesenchymal stem cells into cartilage cells. The cartilage differentiation medium comprised 50 ug/ml ascorbate 2-phosphate, 100 nM dexamethasone, 1% ITS, and 10 ng/ml TGF-beta1. The GAG matrix formation level was fixed by treating the cells in 2D cartilage plate with 10% formaldehyde for 30 minutes, and then the cells were treated with 3% acetic acid solution for 3 minutes, followed by staining with 500 µl Alcian blue (pH 2.5) solution for 30 minutes. The stained sample was washed several times with distilled water and detected using a microscope. In order to obtain quantitative GAG value, the Alcian blue stained plate was left with 3% acetic acid for 10 minutes, and 100 µl of soup was collected to determine O.D. value. This analysis results were supported by FIGS. 2 A, B.

Example 3. Cartilage Stimulation Using Real Time PCR

In order to analyze gene modification between undifferentiated stem cells and cartilage differentiation cells, the expression of cartilage differentiation gene was assessed. For this purpose, Col II and Aggrecan were used as gene markers relating to cartilage cells, and GAPDH was employed as a housekeeping gene. The Real-time PCR was performed as follows. That is, the cells obtained from each group were washed with PBS, and then they were collected with Trypsin-EDTA and RNAs were extracted with TRIzol (Life Technologies, Inc. Grand Island, NY) method. The extracted RNAs 1 µg were used to prepare cDNA, and the change of gene expression was investigated. The primer sets and respective differentiation markers are as shown in Table 1 below.

TABLE 1

| marker | | Sequences | *Origins |
|---|---|---|---|
| Col II | SEQ ID NO. 1 sense | 5'-TTC AGC TAT GGA GAT GAC AAT C-3' | NM_001844 |
| | SEQ ID NO. 2 antisense | 5'-AGA GTC CTA GAG TGA CTG AG-3' | |
| Aggrecan | SEQ ID NO. 3 sense | 5'-GAA TCT AGC AGT GAG ACG TC-3' | NM_013227 |
| | SEQ ID NO. 4 antisense | 5'-CTG CAG CAG TTG ATT CTG AT-3' | |
| GAPDH | SEQ ID NO. 5 sense | 5'-CGG ATT TGG TCG TAT TGG GC-3' | NM_002046 |
| | SEQ ID NO. 6 antisense | 5'-CAG GGA TGA TGT TCT GGA GA-3' | |

*NCBI accession number

The results of the Real-time PCR above were shown in FIG. 2C. After the cartilage differentiation, the cartilage differentiation indicating markers, collagen type II and Aggrecan, significantly increased to higher level, in comparison to the undifferentiated group.

Example 4. 3D Cartilage Organoid Preparation

For the 3D cartilage cells differentiation, 2×10 mesenchymal cells were put into 15 ml polyprophylene tube and were centrifuged at 1,000 rpm for 10 minutes. Thereafter, the cells were incubated at 37° C. for 24 hrs in a 5% $CO_2$ incubator with cartilage differentiation medium to produce 3D spheroid cartilage tissues. Further, natural fusion was induced for the 3D spheroid tissues which contacted to each other. After 24 hrs of incubation, 3D spheroid cartilage tissues were connected to each other to produce 3D spheroid fusion constructs. The obtained 3D spheroid fusion constructs were loaded on a 2D cartilage differentiation cells layer where the cells were in differentiation. Then, cartilage differentiation was continued for 3 weeks to induce self-assembly, while the 2D cartilage differentiation cells layer surrounded the 3D spheroid fusion constructs, and thereby 3D cartilage organoid block was prepared. Further, such 3D organoid block can be spontaneously induced, while connecting different 3D spheroid fusion constructs. To assess the histological features of the 3D cartilage organoid block, the GAG matrix formation level was analyzed after preparing and sectioning paraffin tissue blocks. The method of differentiating mesenchymal cells to 2D cartilage cells layer and the differentiation method and the conditions used for preparing 3D cartilage tissues from 3D spheroid are the same. The cartilage differentiation medium was replaced with new one every 2 days, and the incubation was carried out at 37° C. in 5% $CO_2$ incubator. The cartilage producing medium comprised 50 ug/ml ascobate-2-phosphate, 100 nM dexamethasone, 1% ITS, and 10 ng/ml TGF-beta1. The 3D cartilage organoid preparation method above was carried out as shown in FIG. 3, and resulted in 10 mm×5 mm×4 mm (width×length×height) cartilage tissues were prepared. Further, the 3D cartilage organoid block was confirmed with the Alcian blue staining and collagen type2 gene enhancement.

INDUSTRIAL APPLICABILITY

In this regard, the present invention can be usefully applied to plastic surgery and tissue engineering where cartilage restoration is required, since the cartilage tissues for the medical treatment is prepared in vitro.

The invention claimed is:

1. A method for preparing a 3D cartilage organoid block, which comprises the steps of:
   (a) 3D culturing and differentiating mesenchymal stem cells to produce 3D spheroid cartilage tissues with a differentiation medium containing ascorbate, dexamethasone, and TGF-β;
   (b) 2D culturing and differentiating mesenchymal stem cells to produce a 2D cartilage differentiation cell layer with the differentiation medium;
   (c) preparing 3D spheroid fusion constructs wherein the 3D spheroid cartilage tissues obtained from step (a) are connected to each other;
   (d) loading the 3D spheroid fusion constructs obtained from step (c) on the 2D cartilage differentiation cells layer obtained from step (b);
   (e) incubating the 3D spheroid fusion constructs loaded on the 2D cartilage differentiation cells layer of step (d) to induce self-assembly; and
   (f) forming the 3D cartilage organoid block, wherein the 2D cartilage differentiation cells layer surround the 3D spheroid fusion constructs,
       wherein the 2D cartilage differentiation cells layer is a mesenchymal stem cells layer or a cells layer in the intermediate status of cartilage cell differentiation from mesenchymal stem cells,
       wherein the 3D spheroid fusion constructs are prepared by natural fusion.

2. The method of claim 1, wherein the mesenchymal stem cells include the cells derived from adipose, bone marrow, cord, placenta, synovium, periosteum, perichondrium, tonsil, skin, hair follicle, peripheral blood, muscle, liver, neuron tissue, fetal membrane, amnion, meniscus, or anterior cruciate ligament.

3. The method of claim 1, wherein incubating time under step (d) is 3 weeks.

* * * * *

SEQUENCE LISTING

```
<160> NUMBER OF SEQ ID NOS: 6

<210> SEQ ID NO 1
<211> LENGTH: 22
<212> TYPE: DNA
<213> ORGANISM: Artificial Sequence
<220> FEATURE:
<223> OTHER INFORMATION: Col II marker sense

<400> SEQUENCE: 1
ttcagctatg gagatgacaa tc                                              22

<210> SEQ ID NO 2
<211> LENGTH: 20
<212> TYPE: DNA
<213> ORGANISM: Artificial Sequence
<220> FEATURE:
<223> OTHER INFORMATION: Col II marker antisense

<400> SEQUENCE: 2
agagtcctag agtgactgag                                                 20

<210> SEQ ID NO 3
<211> LENGTH: 20
<212> TYPE: DNA
<213> ORGANISM: Artificial Sequence
<220> FEATURE:
<223> OTHER INFORMATION: Agg rec an marker sense

<400> SEQUENCE: 3
gaatctagca gtgagacgtc                                                 20

<210> SEQ ID NO 4
<211> LENGTH: 20
<212> TYPE: DNA
<213> ORGANISM: Artificial Sequence
<220> FEATURE:
<223> OTHER INFORMATION: Agg rec an marker antisense

<400> SEQUENCE: 4
```

```
ctgcagcagt tgattctgat                                          20

<210> SEQ ID NO 5
<211> LENGTH: 20
<212> TYPE: DNA
<213> ORGANISM: Artificial Sequence
<220> FEATURE:
<223> OTHER INFORMATION: GAPDH marker sense

<400> SEQUENCE: 5
cggatttggt cgtattgggc                                          20

<210> SEQ ID NO 6
<211> LENGTH: 20
<212> TYPE: DNA
<213> ORGANISM: Artificial Sequence
<220> FEATURE:
<223> OTHER INFORMATION: GAPDH marker antisense

<400> SEQUENCE: 6
cagggatgat gttctggaga                                          20
```